(12) United States Patent
Press et al.

(10) Patent No.: US 9,500,614 B2
(45) Date of Patent: Nov. 22, 2016

(54) ELECTRICAL CONDUCTIVITY MODULE

(71) Applicant: Atlas Scientific LLC, Brooklyn, NY (US)

(72) Inventors: Efrem Press, Brooklyn, NY (US); Jon Lindgren, Brooklyn, NY (US); Jordan Press, Brooklyn, NY (US)

(73) Assignee: Atlas Scientific LLC, Brooklyn, NY (US)

( * ) Notice: Subject to any disclaimer, the term of this patent is extended or adjusted under 35 U.S.C. 154(b) by 87 days.

(21) Appl. No.: 14/659,845

(22) Filed: Mar. 17, 2015

(65) Prior Publication Data

US 2015/0260671 A1    Sep. 17, 2015

Related U.S. Application Data

(60) Provisional application No. 61/954,134, filed on Mar. 17, 2014.

(51) Int. Cl.
*G01N 27/06* (2006.01)
*G01N 27/04* (2006.01)

(52) U.S. Cl.
CPC ............ *G01N 27/06* (2013.01); *G01N 27/045* (2013.01)

(58) Field of Classification Search
CPC .............................. G01N 27/06; G01N 27/045
See application file for complete search history.

(56) References Cited

U.S. PATENT DOCUMENTS

| 4,656,427 A | 4/1987 | Dauphinee |
| 6,781,389 B1 | 8/2004 | Colvin et al. |
| 2009/0125250 A1 | 5/2009 | Wang |
| 2011/0316564 A1 | 12/2011 | Park et al. |
| 2013/0234706 A1* | 9/2013 | Mandal ............... G01N 24/081 324/303 |
| 2013/0285579 A1 | 10/2013 | Kawabe et al. |
| 2014/0015551 A1* | 1/2014 | Russ .................... G01N 27/06 324/693 |

OTHER PUBLICATIONS

International Search Report Dated Jun. 18, 2015—International Application No. PCT/US2015/020742.

* cited by examiner

*Primary Examiner* — David Gray
*Assistant Examiner* — Michael Harrison
(74) *Attorney, Agent, or Firm* — Panitch Schwarze Belisario & Nadel LLP

(57) ABSTRACT

A driving circuit for a fluid conductivity sensor includes a pulse width modulation unit, an H-bridge, first and second differential amplifiers, and an analog-to-digital converter (ADC). The pulse width modulation unit generates two opposing driving signals. The H-bridge receives the two opposing driving signals and generates two H-bridge outputs. The first differential amplifier includes first inputs connected in parallel to a shunt resistor. One of the first inputs is coupled to the two generated H-bridge outputs. The second differential amplifier includes second inputs connected in parallel with a pair of terminals having a sensor attached thereto. One of the second inputs and the pair of terminals receive a signal from the other of the two generated H-bridge outputs. The ADC receives a first output representative of a first current from the first differential amplifier; and a second output representative of a second current from the second differential amplifier.

20 Claims, 3 Drawing Sheets

ELECTRICAL CONDUCTIVITY MODULE

CROSS-REFERENCE TO RELATED APPLICATIONS

This application claims the benefit of U.S. Provisional Patent Application No. 61/954,134, filed on Mar. 17, 2014, entitled "Electrical Conductivity Module," the entire contents of which are incorporated herein by reference in their entirety.

BACKGROUND OF THE INVENTION

Embodiments of the present invention relate to fluid conductivity sensors, and more particularly, to a driving circuit for a fluid conductivity sensor.

High end sensors for detecting the electrical conductivity of a fluid, particularly an aqueous solution, in which the sensor is submerged have existed for some time. However, such devices suffer from numerous difficulties, particularly where the ultimate determination by the sensor is subsequently used in robotics or other embedded systems.

When measuring the conductivity of an aqueous solution, one difficulty encountered is the potential to contaminate the sensor's electrodes (called "fouling"). This occurs when a current is passed through the sensor's electrodes, which causes ions to collect at both the anode and cathode. Sufficient collection of these ions alters the measurements, due to ionic interference in the conductivity of the fluid under test.

Existing methods for measuring conductivity of an aqueous solution typically utilize a voltage swing across a single electrode. This voltage swing (typically from a fixed positive potential (+X volts) to the same negative voltage (−X volts)) reverses the attraction of the ions at the electrodes, thus preventing fouling. This method, however, requires a wide range of voltages. Typically, these voltages are arrived at through a voltage inverter, which increases the energy use of the circuit, increases the complexity of the circuit (e.g., the negative voltage must be regulated), increases the size of the circuit, and increases noise in the circuit.

Existing methods also do not make sufficient use of modern microcontrollers. Instead, a significant amount of the circuit is typically dedicated to the measurement and interpretation of the results. Examples of this would be compensating for op-amp parameters (such as input bias current, offset voltage, or the like). The result is increased power consumption with decreased sensitivity and accuracy.

Finally, existing methods typically provide data in ways which are difficult to integrate into robotics or other embedded systems. For example, the conductivity sensor output may be presented as 4-20 mA current loops (i.e., analog) or via a digital display. Both of these are difficult, if not impossible, to integrate into the vast array of modern systems which expect a digital output (such as other microcontrollers, computer monitoring systems, dataloggers, or the like).

It is therefore desirable to provide a driving circuit for a fluid conductivity sensor that enables a simpler method of obtaining measurement results, decreases power requirements, increases sensitivity and accuracy, and provides data in a digital form that can be transferred and utilized by further systems.

SUMMARY OF INVENTION

Embodiments of the present invention include a driving circuit for a fluid conductivity sensor. The driving circuit includes a pulse width modulation unit, an H-bridge, first and second differential amplifiers, and an analog-to-digital converter (ADC). The pulse width modulation unit is configured to generate two opposing driving signals. The H-bridge is configured to receive the two opposing driving signals and generate at least two H-bridge outputs. The first differential amplifier includes first inputs connected in parallel to a shunt resistor. One of the first inputs is coupled to one of the at least two generated H-bridge outputs. The second differential amplifier includes second inputs connected in parallel with a pair of terminals having a sensor attached thereto. One of the second inputs and the pair of terminals are configured to receive a signal from the other of the at least two generated H-bridge outputs. The analog-to-digital converter (ADC) is configured to receive: a first output representative of a first current from the first differential amplifier; and a second output representative of a second current from the second differential amplifier.

BRIEF DESCRIPTION OF THE DRAWINGS

The following detailed description of a preferred embodiment of the invention, will be better understood when read in conjunction with the appended drawings. For the purpose of illustration, there is shown in the drawings an embodiment which is presently preferred. It should be understood, however, that the invention is not limited to the precise arrangements and instrumentalities shown.

DETAILED DESCRIPTION OF THE INVENTION

Figure 1:
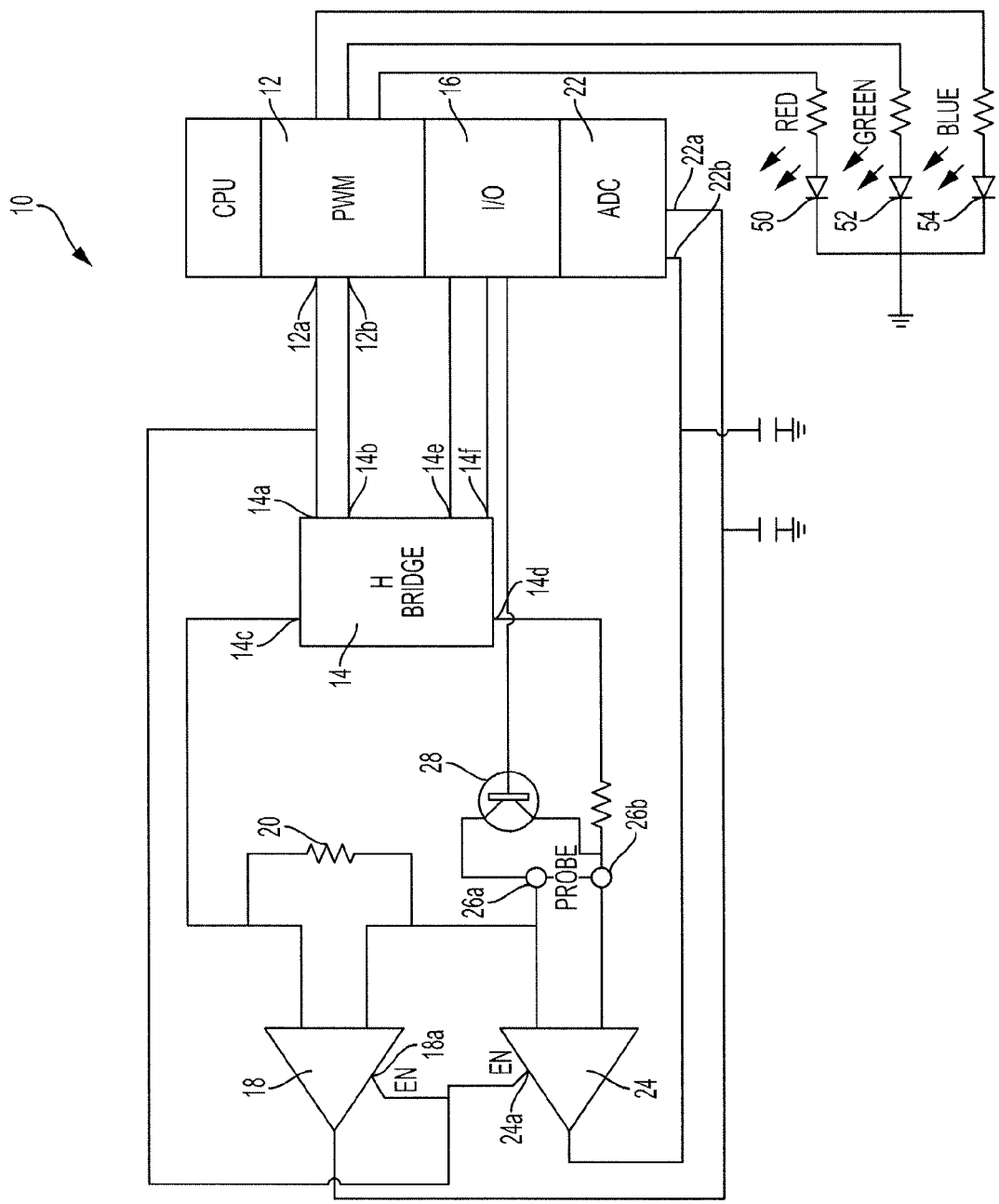
FIG. 1 is a schematic view of a driving circuit in accordance with a preferred embodiment of the present invention.

Certain terminology is used in the following description for convenience only and is not limiting. The words "right", "left", "lower", and "upper" designate directions in the drawings to which reference is made. The words "inwardly" and "outwardly" refer to directions toward and away from, respectively, the geometric center of the device and designated parts thereof. The terminology includes the above-listed words, derivatives thereof, and words of similar import. Additionally, the words "a" and "an", as used in the claims and in the corresponding portions of the specification, mean "at least one."

Referring to the drawings, wherein like numerals indicate like elements throughout, there is shown in FIG. 1 a driving circuit 10 for use with a conductivity sensor (not shown) in accordance with a preferred embodiment of the present invention. The circuit 10 includes a pulse width modulation (PWM) unit 12 having a pair of driving outputs 12a, 12b. The PWM unit 12 generates a first driving signals and a second, complementary (i.e., opposite) driving signal which may be respectively emitted at the driving outputs 12a, 12b. The first and second driving signals each preferably exhibit a frequency in the range of about 4 kHz and a duty cycle of 50%, although the frequency, duty cycle, and other characteristics may be varied as desired.

The driving outputs 12a, 12b of the PWM unit 12 are preferably coupled to corresponding inputs 14a, 14b of an H-bridge 14, which further includes two outputs 14c, 14d and two feedback channels 14e, 14f, which return information regarding the timing of the H-bridge to an input/output (I/O) unit 16. The H-bridge 14 is used to alternately reverse the polarity of the signal applied to the sensor, and the I/O unit 16 uses the timing of the H-bridge 14 to coordinate the sampling of signals from the sensor, as will be described in more detail below.

Once output 14c of the H-bridge 14 is directed to a combination of a first differential amplifier 18 having its inputs connected across a shunt resistor 20. The shunt resistor 20 preferably has a resistance in the range of about 100 (Ω). However, other resistances may be used as well in keeping with the invention. The differential amplifier 18 also receives the signal output by the PWM unit 12 as an enable input 18a. The differential amplifier 18 outputs the current across the shunt resistor 20, which is fed back to the input 22a of an analog-to-digital (ADC) 22. By knowing the fixed resistance of the shunt resistor 20 and the current through the shunt resistor 20, the voltage being applied may be determined.

Another output 14d of the H-bridge is coupled to a combination of a second differential amplifier 24 having its inputs connected across a pair of terminals 26a, 26b to which the sensor is connected. The terminals 26a, 26b may comprise posts, sockets, coaxial receptacles or the like types of electrical connectors. A transistor 28 may be coupled across the terminals 26a, 26b and receive an output from the I/O unit 16 as a gating signal for controlling operation of the sensor. In light of embodiments of the disclosure described hereinthroughout, one of ordinary skill in the art would understand that the transistor 28 as well as the output connected thereto, from the I/O unit 16 may be removed.

The second differential amplifier 24 also receives the signal output by the PWM unit 12 as an enable input 24a, and outputs the current across the sensor through the terminals 26a, 26b. The current reading is fed back to another input 22b of the ADC 22. With the current across the sensor and the previously determined supply voltage from the measurement across shunt resistor 20, the resistance through the fluid encountered by the sensor can be determined. The conductance of the fluid is then determined by the inverse of the calculated resistance.

The PWM unit 12, the I/O unit 16, and the ADC 22 are preferably part of, or at least controlled by, a central processing unit (CPU) 30. The CPU 30 may be a microcontroller, a microprocessor, application specific integrated circuit (ASIC), or the like. For example, one or more of the PWM unit 12, the I/O unit 16, and the ADC 22 may reside within the CPU 30 such that the inputs and outputs described above may be in the form of pins (not shown) of the CPU 30. Still further, one or more of the PWM unit 12, the I/O unit 16, and the ADC 22 may be circuits externally located from the CPU 30 and may be coupled thereto via traces, wires, or other like electrical connectors (not shown). The CPU 30, for example, may control power supplied, settings and parameters, and facilitate communications for the PWM unit 12, the I/O unit 16, and the ADC 22.

It is preferred that at least the H-bridge 14, the first and second differential amplifiers 18, 24, the shunt resistor 20, and the terminals 26a, 26b are commonly housed. The housing (not shown) may also contain the PWM unit 12, the I/O unit 16, the ADC 22 and/or the CPU 30, as desired.

Figure 2:
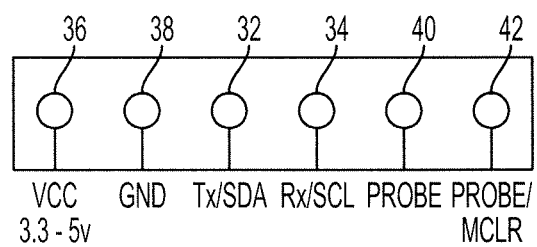
FIG. 2 is a schematic view of a header pin arrangement for the circuit of FIG. 1.

The data obtained from the sensor is preferably passed from the circuit 10 to an external circuit (not shown) using common methods, such as universal asynchronous receiver/transmitter (UART) protocols (e.g., RS-232, TTL serial, RS-422, RS-485, or the like), inter-integrated circuit ($I^2C$) protocol, or the like. Referring to FIG. 2, a pair of transmitter and receiver pins 32, 34 are preferably provided to enable communication with the external circuit, as described above. Power and ground pins 36, 38 may also be provided. In addition, probe pins 40, 42 may be provided for connecting the sensor to the terminals 26a, 26b.

Referring again to FIG. 1, LEDs 50, 52, 54 are preferably provided for indicating a status of the circuit 10 to the user. For example, a red LED 50 may be provided as an error indicator. A green LED 52 may be provided to indicate that communication is occurring pursuant to a UART protocol. Similarly, a blue LED 54 may be provided to indicate that communication is occurring pursuant to $I^2C$. Although LEDs are used in the embodiment shown, other types of indicators, including alphanumeric displays, aural indicators, or the like may also be used. In addition, other conditions of the device 10 and/or the sensor may be communicated to the user.

Operation of the circuit 10 will now be described. Upon initialization, the PWM unit 12 may begin generation of the driving signals. However, the outputs 12a, 12b thereof and the H-bridge 14 are preferably initially disabled. To read, the outputs 12a, 12b of the PWM unit 12 and H-bridge 14 are enabled. The H-bridge 14 works to constantly reverse the polarity applied to the terminals 26a, 26b. The first and second differential amplifiers 18, 24 are alternately enabled to output samplings to the ADC 22, such that the currents are alternately read from the shunt resistor 20 and the terminals 26a, 26b.

Preferably, the ADC 22 receives sixteen samples from each of the first and second differential amplifiers 18, 24. The samples may be low-pass filtered, oversampled, and the like by the ADC 22 and/or the CPU 30. Average readings for the shunt resistor 20 and the sensor are generated and used to determine the conductance of the fluid in which the sensor is submerged. The conductivity is determined in the ADC 22 and/or the CPU 30 by the conductance in combination with the K factor of the sensor, and may be temperature compensated. Finally, the conductivity is emitted to the external circuit.

Figure 3:
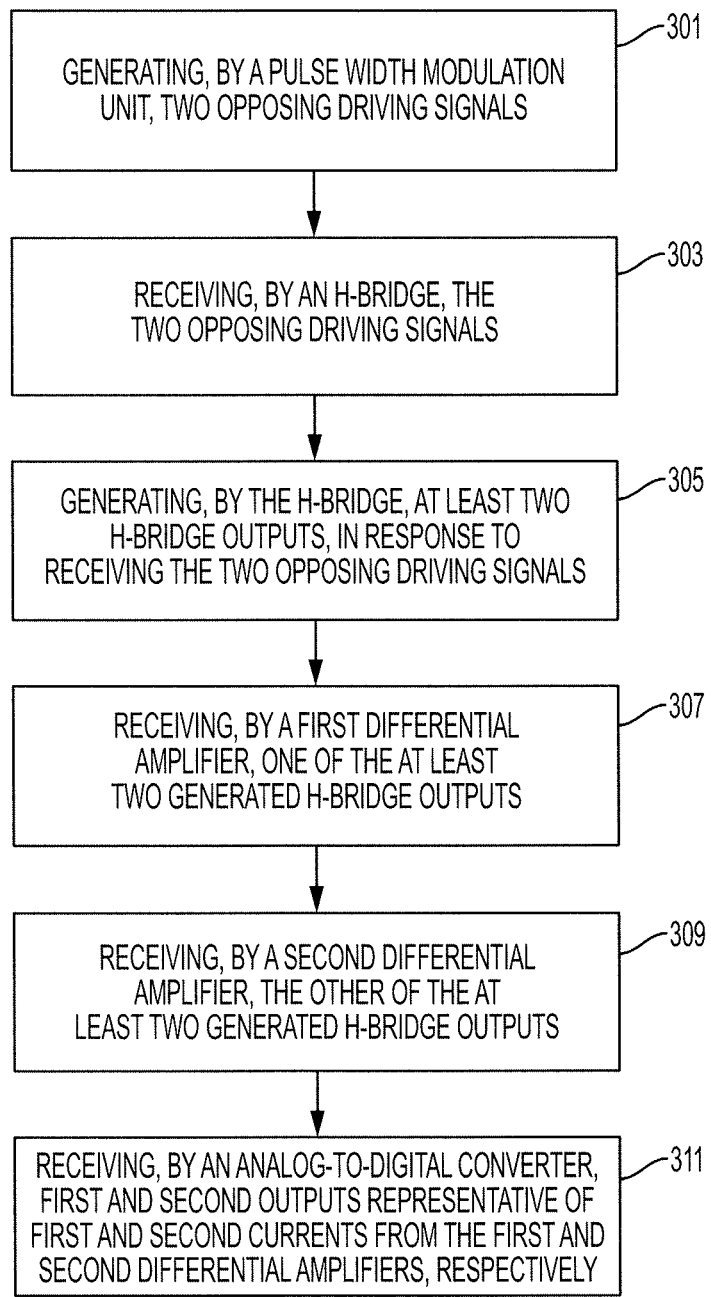
FIG. 3 is a flow diagram of a method of one embodiment of a method for driving a fluid conductivity sensor.

FIG. 3 is a flow diagram of one embodiment of a method for driving a fluid conductivity sensor. The method may comprise a number of steps which may be performed in any suitable order. Step 301 comprises generating, by a pulse width modulation unit, two opposing driving signals. Step 303 comprises receiving, by an H-bridge, the two opposing driving signals. Step 305 comprises generating, by the H-bridge, at least two H-bridge outputs, in response to receiving the two opposing driving signals. Step 307 comprises receiving, by a first differential amplifier, one of the at least two generated H-bridge outputs. Step 309 comprises receiving, by a second differential amplifier, a signal from the other of the at least two generated H-bridge outputs. Step 311 comprises receiving, by an analog-to-digital converter, first and second outputs representative of first and second currents from the first and second differential amplifiers, respectively.

From the foregoing, it can be seen that embodiments of the present invention comprise sensing circuits for electrochemical sensors. It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A driving circuit for a fluid conductivity sensor, the circuit comprising:
a pulse width modulation unit configured to generate two opposing driving signals;
an H-bridge configured to:
receive the two opposing driving signals; and
generate at least two H-bridge outputs;
a first differential amplifier including first inputs connected in parallel to a shunt resistor, wherein one of the first inputs is configured to receive one of the at least two generated H-bridge outputs;
a second differential amplifier including second inputs connected in parallel with a pair of terminals having a sensor attached thereto, wherein one of the second inputs and the pair of terminals are configured to receive the other of the at least two generated H-bridge outputs; and
an analog-to-digital converter (ADC) configured to receive:
a first output representative of a first current from the first differential amplifier; and
a second output representative of a second current from the second differential amplifier.

2. The driving circuit of claim 1, further comprising a processor configured to control at least one of the pulse width modulation unit and the ADC.

3. The driving circuit of claim 1, further comprising an input/output unit configured to control operation of the sensor.

4. The driving circuit of claim 1, further comprising one or more indicators configured to indicate an operating status of the driving circuit.

5. The driving circuit of claim 1, wherein the ADC is configured to alternately receive samples from each of the first and second outputs.

6. The driving circuit of claim 5, wherein the processor is configured to determine a fluid conductivity based at least in part on the received samples.

7. The driving circuit of claim 6, further comprising a transceiver configured to communicate the fluid conductivity to a circuit remote to the driving circuit.

8. A driving circuit for a fluid conductivity sensor, the circuit comprising:
a pulse width modulation unit configured to generate two opposing driving signals;
an H-bridge configured to:
receive the two opposing signal; and
generate at least two H-bridge outputs;
a first differential amplifier including first inputs connected in parallel to a shunt resistor, wherein one of the first inputs is coupled to one of the at least two generated H-bridge outputs;
a second differential amplifier including second inputs connected in parallel with a pair of terminals having a sensor attached thereto, wherein one of the second inputs and the pair of terminals are configured to receive a signal from the other of the at least two generated H-bridge outputs; and
an analog-to-digital converter (ADC) configured to alternately receive samples from each of a first output representative of a first current from the first differential amplifier; and a second output representative of a second current from the second differential amplifier.

9. The driving circuit of claim 8, further comprising an input/output unit configured to control operation of the sensor.

10. The driving circuit of claim 8, wherein at least two of the pulse width modulation unit, the H-bridge, the first differential amplifier, and the second differential amplifier are commonly housed.

11. The driving circuit of claim 8, further comprising a processor configured to determine a fluid conductivity based at least in part on the received samples.

12. The driving circuit of claim 11, further comprising a transceiver configured to communicate the fluid conductivity to a circuit remote to the driving circuit.

13. The driving circuit of claim 11, wherein the processor is configured to control at least one of the pulse width modulation unit and the ADC.

14. The driving circuit of claim 8, further comprising one or more indicators configured to indicate an operating status of the driving circuit.

15. A driving circuit for a fluid conductivity sensor, the circuit comprising:
a pulse width modulation unit configured to generate two opposing driving signals;
an H-bridge configured to:
receive the two opposing signal; and
generate at least two H-bridge outputs;
a first differential amplifier including first inputs connected in parallel to a shunt resistor, wherein one of the first inputs is coupled to one of the at least two generated H-bridge outputs;
a second differential amplifier including second inputs connected in parallel with a pair of terminals having a sensor attached thereto, wherein one of the second inputs and the pair of terminals are configured to receive a signal from the other of the at least two generated H-bridge outputs;
an analog-to-digital converter (ADC) configured to alternately receive samples from each of a first output representative of a first current from the first differential amplifier; and a second output representative of a second current from the second differential amplifier; and
a processor configured to determine a fluid conductivity based at least in part on the received samples.

16. The driving circuit of claim 15, wherein at least two of the pulse width modulation unit, the H-bridge, the first differential amplifier, and the second differential amplifier are commonly housed.

17. The driving circuit of claim 15, further comprising a transceiver configured to communicate the fluid conductivity to a circuit remote to the driving circuit.

18. The driving circuit of claim 15, further comprising an input/output unit configured to control operation of the sensor.

19. The driving circuit of claim 18, wherein the H-bridge is further configured to convey timing information to the input/output unit.

20. The driving circuit of claim 19, wherein the input/output unit uses the timing information to control a sampling of one or more signals from the sensor.

* * * * *